(12) United States Patent
Thys

(10) Patent No.: US 10,661,001 B2
(45) Date of Patent: May 26, 2020

(54) APPARATUS AND METHOD FOR SUPPORTING AN OPERATOR IN OPERATING A MEDICAL DEVICE AS WELL AS SINGLE-USE ITEMS FOR A MEDICAL DEVICE

(75) Inventor: Martin Thys, Grettstadt (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 1194 days.

(21) Appl. No.: 13/403,374

(22) Filed: Feb. 23, 2012

(65) Prior Publication Data

US 2012/0211422 A1 Aug. 23, 2012
US 2013/0206693 A2 Aug. 15, 2013

Related U.S. Application Data

(60) Provisional application No. 61/445,597, filed on Feb. 23, 2011.

(30) Foreign Application Priority Data

Feb. 23, 2011 (DE) .......................... 10 2011 004 620

(51) Int. Cl.
*A61M 1/14* (2006.01)
*A61M 1/36* (2006.01)

(52) U.S. Cl.
CPC .............. *A61M 1/14* (2013.01); *A61M 1/367* (2013.01); *A61M 1/3621* (2013.01); *A61M 2205/502* (2013.01); *A61M 2205/581* (2013.01); *A61M 2205/582* (2013.01); *A61M 2205/583* (2013.01); *A61M 2205/587* (2013.01)

(58) Field of Classification Search
None
See application file for complete search history.

(56) References Cited

U.S. PATENT DOCUMENTS

| 4,471,412 A | 9/1984 | Mori |
| 6,029,503 A | 2/2000 | Sumioki |
| 2005/0171492 A1* | 8/2005 | Rodriquez .............. A61M 5/14 604/264 |
| 2007/0106263 A1 | 5/2007 | Ward |
| 2008/0173308 A1 | 7/2008 | Schermeier et al. |
| 2009/0012449 A1 | 1/2009 | Lee et al. |
| 2009/0294339 A1 | 12/2009 | Biewer et al. |

FOREIGN PATENT DOCUMENTS

| EP | 1 195 171 | 4/2002 |
| EP | 1 676 539 | 7/2006 |
| EP | 1 872 814 | 1/2008 |

* cited by examiner

*Primary Examiner* — Michael J Felton
*Assistant Examiner* — Katherine A Will
(74) *Attorney, Agent, or Firm* — Jacobson Holman, PLLC.

(57) ABSTRACT

An apparatus for supporting an operator in operating a medical device has a signaling device that signals a necessary operation of a component to be operated of the medical device. The signaling device emits a signal from the component to be operated and/or orients a signal onto the component to be operated. The signaling device emits at least one of an optical, an acoustical, and a haptical signal. The apparatus also includes a control apparatus that controls the signaling device based on the component operation to be performed, with the control by the control apparatus being independent of an operator request.

22 Claims, 6 Drawing Sheets

APPARATUS AND METHOD FOR SUPPORTING AN OPERATOR IN OPERATING A MEDICAL DEVICE AS WELL AS SINGLE-USE ITEMS FOR A MEDICAL DEVICE

CROSS-REFERENCE TO RELATED APPLICATION

This application claims the benefit of U.S. provisional application No. 61/445,597, filed Feb. 23, 2011, and the priority of German application number 10 2011 004 620.8, filed Feb. 23, 2011, hereby incorporated by reference.

BACKGROUND OF THE INVENTION

1. Field of Invention

The present invention relates to a device and a method for supporting an operator in operating a medical device, a medical device, as well as a single-use item for a medical device.

2. Description of the Prior Art

Frequently, the operation of medical devices with all its components is complex and can only be performed safely following training or extensive auto-tutorial studies of operating manuals. This, for example, is the case in the field of blood treatment devices, in particular for dialysis apparatus, such as hemodialysis apparatus, peritonealdialysis apparatus, hemofiltration apparatus, or hemodiafiltration apparatus, apheresis apparatus, or also for other medical devices, for example, for administering of medication.

For these medical devices, single-use items must frequently be exchanged, which comprise specific components connected to the medical device. Examples of such single-use items are input hoses for the patient blood, bags for dialysate, filters in a dialysis apparatus, or syringes for dosing of medicaments, which comprise components connected to the medical device in the form of hose connectors, mounts for filters, hose sections for insertion into peristaltic pumps, syringe nozzles, syringe plungers, etc. For exchanging these single-use items in the medical device and for operation of the individual components of the respective single-use items, a specific order of the manipulations to be performed must frequently be obeyed.

Although the corresponding medical devices of different types differ in principle, yet the components to be operated are frequently similar. Correspondingly, an operator who is familiar with the principal function of such a medical device may also find his way around in a similar medical device of another type by studying a brief operation manual relatively quickly.

For said medical devices, in particular for medical devices for blood treatment, interactions of an operator with the medical device are necessary at least before and/or during and/or following the treatment of the respective patient in order to prepare the medical device for the treatment of the patient, to maintain the operation, and/or to reset the medical device into an initial state for performing a treatment of another patient following the treatment.

For example, for blood treatment apparatus, connections of the medical devices with the bloodstream of the patient must be established, which typically comprises connecting one hose a time with the venous and the arterial access of the patient. Further, in the blood treatment apparatus, single-use items or consumable items, through which the blood flows, must be inserted and removed following the treatment; the blood treatment apparatus must be supplied with corresponding fluid supplies and gas supplies, and supplemental substances must be supplied or led away. The components directly connected to the patient are typically single-use items comprising these components or disposable items, which must be newly installed for each patient and which are removed and disposed following the treatment. These single-use items are, for example, the hoses which connect the blood stream of the patient with the medical device, the supply lines within the medical device, the filter membrane, as well as the bag for taking up the dialysate. Correspondingly, during the operation of the medical device, for each new patient, routine steps must be performed which, following the training of the respective operating personnel, can be easily performed by the latter.

However, individual training must be performed for each design type. Thereby, mix-ups or confusion may easily arise on the operator's side if an operator has to administrate medical devices of different designs successively or simultaneously.

Correspondingly, for the at some parts very extensive operating procedures, specially trained qualified personnel is frequently required because only they possess the knowledge, skills and practical experience required for time critical operating actions at the medical device to be able to perform the correct operating action, if necessary, even without studying the operator manual again. In this context, it is known to output corresponding text and image based operating instructions on a device monitor of the medical device. For such text and image based operating instructions, which are output by the medical device on a monitor, it is, however, necessary to either display the individual components at which the operating steps should be performed, or assign a meaning to them. Then, the operator must correlate the actual component to be operated to the image and/or the instruction given in text form. Thereby, severe mistakes may occur because texts and/or images on the device monitor may be misinterpreted and operating actions may correspondingly be performed on another component than the one actually meant.

Further, for medical devices provided for home use it cannot be assumed that a patient himself builds up the expertise that may be necessary for operating a medical device.

Correspondingly, a medical device should be safely and intuitively operable by an operator within a training that is as short as possible. It would be desirable if the individual procedures to be performed by each operator could be always performed safely and completely, independently of respective state of experience and knowledge. Because the medical devices rely on the manipulation of operators, for example for exchanging the single-use components, an interaction between an operator and the medical device cannot be forgone in any case.

SUMMARY OF THE INVENTION

The problem to be solved by the present invention therefore is to provide an apparatus for supporting an operator in operating a medical device, wherein the safety of the operation of the medical device is increased.

This problem is solved by an apparatus for supporting an operator in operating a medical device with the features that are described herein. Preferred embodiments of the invention are also described herein.

Correspondingly, the apparatus comprises a signaling device for signaling a necessary operation of a component to be operated of the medical device, preferably by emitting a signal from the component to be operated and/or by orienting a signal onto the component to be operated.

By using the signaling device for signaling a necessary operation of a component to be operated, the operator's attention is called towards and the operator is guided towards the component to be operated so that the operator directly incorporates this component to be operated in the next operating step. Thereby, it is achieved that the attention of the operator is guided towards the component to be operated and the danger of an operating error is reduced.

Therefore, for the operation of the medical device an intuitive operation results, which correspondingly prompts the respective operation by means of the subjective perception of the signaling output by the signaling device without calling for cognitive efforts on the side of the operator. Correspondingly, the operator is induced to perform an action step or an action by the signaling, which can be suggestively/intuitively immediately perceived, and may perform the correct operation of the medical device. This is significant both with regard to safety aspects and with regard to efficiency aspects because own considerations of the operator, in particular, during standard routines, may be eliminated to a large extent and the operator performs the correct operation spontaneously and immediately. In contrast to this, logical considerations and drawing up of conclusions require time and such considerations or drawing up of conclusions are error prone, in particular under the time pressure or stress that often prevails in the medical field.

By the signaling of the component to be operated by the signaling device, it is further ensured that even when an operating manual is not available in which the necessary operating steps are documented, the necessary operating step may nevertheless be performed. A continued availability of operating manuals is not always given because they may be kept locally separated from the actual medical device. However, for medical devices, in particular for the abovementioned blood treatment apparatus, specific operating procedures must be strictly obeyed in view of both their order and their completeness because they may be safety relevant and an erroneous operation may result in an impairment of the patient, of the surrounding, and/or the apparatus. Further, providing well-trained skilled personnel is cost-intensive and disadvantageous in view of economic aspects.

By means of the signaling unit and its specific actuation when an operation is necessarily to be performed, a simplification of the operation of the medical device is obtained because the achieved intuitive operation may be performed significantly quicker and more intuitively by the operator, particularly in time critical or stress afflicted-situations and the danger of an operating error may be reduced correspondingly. Correspondingly, the cognitive requirements for the operator relating to retention, combinatorial skills, and concentration are reduced. In particular, the steps of the mechanical preparation of a medical device, such as the insertion of the respective single-use components into the medical device as well as the post-processing of the medical device, namely the removal and disposal of the single-use components, may also be performed by personnel that is to a large extent untrained.

Further, the signaling by the signaling device at the component to be operated is advantageous for the reason that the operator may entirely focus on the at some parts demanding and complex mechanical manipulations of the components to be operated of the medical device because his visual attention does not have to be removed from the component; instead, both the signal and the component may be kept within the field of view caused by the signaling at the component.

In a case, in which the operator must be able to verify the correct operation or manipulation of a component by checking a state of the component at a location different from the component itself, the component itself may further emit haptic information, for example, vibrations, in order to submit a certain operation state of the component to the operator while he has his view oriented towards somewhere else. For example, during interlocking two components in a specific orientation, the operator may verify the impermeability of the components on the system display. Here, a haptic feedback may be delivered via a vibration if the components are interlocked in the proper orientation while the operator verifies the impermeability of the interlocked components on the system display.

In this context, the term "component to be operated" is to be interpreted as a component of the medical device which must be subjected to an operating step of an operator. This may be, on the one hand, input devices such as buttons, switches, touch screens etc, and on the other hand, mainly mechanical components such as operation of hose clips, pumps etc. Further, the term is to be interpreted as relating to components of single-use items, such as supply hoses, filters, media supplies, dialysate bags, syringes etc, which comprise corresponding connectors, nozzles, hose sections, clips etc as components to be operated. Therefore, the components to be operated are to be interpreted as any components to be operated that are necessary for the operation of the medical device.

The signaling device may comprise an optical, haptical, and/or acoustical signal generator for generating an optical, haptical, and/or acoustical signal. In this way, an optical, haptical, and/or acoustical signal may be selectively output at the respective component to be operated. Further, an information may be output at the component itself by means of the signaling generator by the arrangement of according optical, haptical, or acoustical signal generators, for example, by means of a symbol or different symbols, by means of different acoustical or haptical signals, or by means of the display of text. These signals may be correlated with the information output at the device display of the medical device. In particular, the operator may read additional information, for instance texts, at the device display and relate these to symbols signaled at the respective components.

The signaling device may be a projector that illuminates the component to be operated so that the component to be operated emits a signal in the form of reflected light. Hereby, an illumination and the emission of a signal may efficiently be achieved. The signaling device may also be a light source provided in the component to be operated, preferably an LED. Furthermore, the signaling device may be an electrodynamical or electro-acoustical converter which interacts with the component to be operated and/or is provided thereon. At least in the case of the projector as well as in the case of the electrodynamical converter, the signaling device may interact with the component to be operated in order to emit the signal from the component.

For obtaining the intuitive information of the operator with respect to the component to be operated, the signal of the signaling device originates from the component to be operated. This may either be achieved in that the component itself emits an optical, haptical, or acoustical signal by, for example, being designed itself with a light source or an optical apparatus in such a way that light coupled-in emerges at a specific location of the component from the component, that a vibration generator is provided in the component, or an acoustic signal generator, or, however, in that the component to be operated is specifically illuminated from outside by means of an illumination generator and the component emits a signal by means of reflection of the light.

In particular, in the field of single-use items, the components may comprise a light guide and/or may be designed as a light guide, wherein light may be coupled into the component via the signaling device and an optical signal may be correspondingly uncoupled from the single-use item in order to send a signal to the operator. In this way, an elaborate construction of the single-use item may be forgone.

In order to provide the operator with certain information, the signaling device may be designed for activation of at least one of the optical symbols provided at the component to be operated. Preferably, the signaling device is designed for selective activation of at least two of the optical symbols arranged at the component to be operated. In this way, changing states, for example, the transition from an incomplete interlock of two components to a complete interlock of two components, may also be communicated to the operator.

By means of a control apparatus for controlling the signaling device in dependency of the operation to be performed, an operation order of different components may be provided to the operator. This is preferably independent of an operator request—the operator does not have to request the control apparatus for outputting the signaling; instead, it is the control apparatus which requests the operator for performing an action. For this purpose, the control apparatus is preferably connected with the system monitor of the medical device and may react according to the system states of the medical device and request the operator for according actions.

A medical device including the apparatus as described above, preferably a dialysis device, a hemodialysis device, a hemofiltration device, a hemodiafiltration device, a peritonealdialysis device or an apheresis device also solves the objective.

The abovementioned problem is also solved by a method for supporting an operator in operating a medical device with the features that are described herein.

Correspondingly, the operator's attention is called towards a component to be operated of the medical device by signaling a necessary operation of a component to be operated of the medical device by means of emitting a signal from the component to be operated and/or by orienting a signal onto the component to be operated. Thereby, the component may emit an optical, acoustical, and/or haptical signal, wherein an optical symbol may be emitted from the component to be operated, preferably, an optical signal selected from at least two optical signals arranged at the component be operated.

Further, the above mentioned problem is solved by a single-use item of a medical device with the features that are described herein.

Correspondingly, the component to be operated comprises a signaling device for emitting an optical, acoustical, and/or haptical signal. In this way, the above-mentioned advantageous effects may also be achieved for single-use items for the medical device.

Thereby, the components may comprise a light source, preferably, an LED, and/or an electrodynamical or electroacoustical converter as a signaling device. Furthermore, the component may comprise a light guide and/or be designed as a light guide, wherein the light guide comprises an interface for coupling-in of light of a signaling device of an apparatus for supporting an operator. Thereby, at least one optical symbol for emitting an optical signal may be provided, but preferably at least two optical symbols that may be selectively activated. The component may also be designed as a single-use item and may preferably be designed as a disposable item of the medical device.

Preferably, the signaling device is a part of the medical device and, in particular, integrated in the main part of the medical device, integrated in a single-use item, or provided as an item separate and removable from the conventional single-use items.

BRIEF DESCRIPTION OF THE DRAWINGS

In the following, preferred embodiments of the present disclosure are described with regard to the following Figures.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
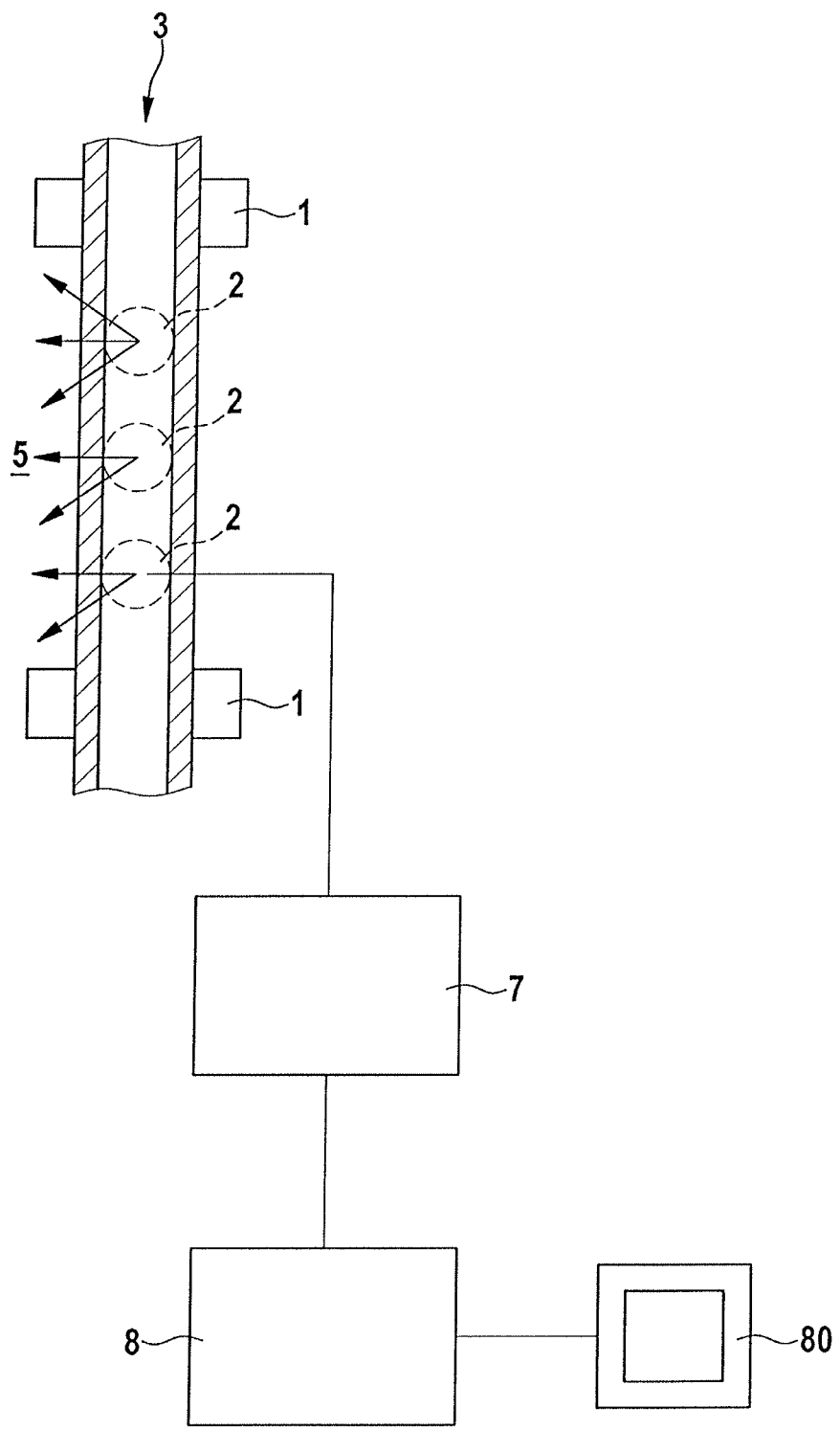
FIG. 1 shows a component in the form of a blood hose, which is held in the medical device.

FIG. 1 schematically shows a system hose 3 of a medical device, which is configured as a single-use item. This system hose 3 is clamped into the mount 1 at the main part of the medical device and is held thereby.

A signaling device 2 is provided which is arranged in the medical device so that the component to be operated, namely the system hose 3 in this case, emits a signal. Here, this signal is illustrated in the form of light which is schematically indicated as the arrows 5 and which originates from the system hose 3. The signaling device 2 correspondingly signals to the operator that an operating manipulation is necessary at the system hose 3. Such an operating manipulation may, for example, be the necessary exchange of the system hose 3.

In the shown embodiment the signaling device 2 is formed in the form of light sources, preferably LEDs, which are arranged in the medical device so that they are arranged behind the system hose 3 in such a way that, upon activation of the light sources 2, the system hose 3 is illuminated so that it seems to shine itself at least in some parts by means of the diffusive scattering of the emitted light at the surface of the hose as well as by means of the transmission of the light through the hose, and the hose 3 correspondingly outputs a signal to the operator.

The signaling device 2 in the form of a light source is connected with a control apparatus 7. The control apparatus 7 controls the signaling device 2 so that the signaling device is activated whenever an operator's attention should be called towards the fact that an action should be performed with the component to be signaled with the signaling device 2, the system hose 3 in this case. For example, in the case shown in FIG. 1, it may be signaled that the system hose 3 has not been inserted properly in the mount 1, or it may be signaled that the system hose 3 should be removed from the mount 1, or it may be signaled that the system hose 3 should be replaced and correspondingly removed from the mount 1.

Preferably, the signaling device 2 or the control apparatus 7 is communicatively connected with a system monitor 8 of the medical device. The system monitor 8 of the medical device monitors the medical device as well as the states in the medical device and may correspondingly inform the control apparatus when an alert state exists or when a situation exists, in which an operating action is necessary.

The system monitor 8 may further output information to the operator at another user interface, for example, a monitor 80, with regard to the present state of the medical device and/or with regard to further necessary operator steps. By means of the simultaneous output of information, for example text information or pictograms or a combination thereof, on the monitor 80 by the system monitor 8 and the simultaneous signaling of a component to be operated via the signaling device 2 via the control apparatus 7, on the one hand, an explanation of the action to be performed is delivered to the operator, and, on the other hand, the operator is directly intuitively guided to the component at which an action must be performed.

Thereby, the type of signaling device 2 may be adapted to the respective requirements and constructional constraints of the medical device.

For example, in FIG. 2 again, a system hose 3 is clamped between a bearing point/mounting point 1 and a clip 10, i.e. a manually operated clip apparatus. A clip lever 12, which is pivotable around an axis of rotation 14 and pre-stressed in clamping direction by means of a spring, correspondingly clamps the system hose 3.

In case an operator manipulation should be necessary at this clip apparatus or this clip lever, this will be signaled via a signaling device. Here, the signaling device 2 is a multi-part design and comprises a projector 20 and a projector surface 22, which is provided at the clip lever 12. Correspondingly, the projector 20 is controlled via the control apparatus 7 if it should be signaled to the operator that the component in the form of the clip apparatus 12 should be operated. The projector 20 then projects a corresponding symbol or merely an illumination onto the projection surface 22 of the clip lever 12 so that light signals 5 are emitted in turn, which may be perceptible by the operator. Correspondingly, the operator is directly guided to the operation of the clip lever.

Figure 2:
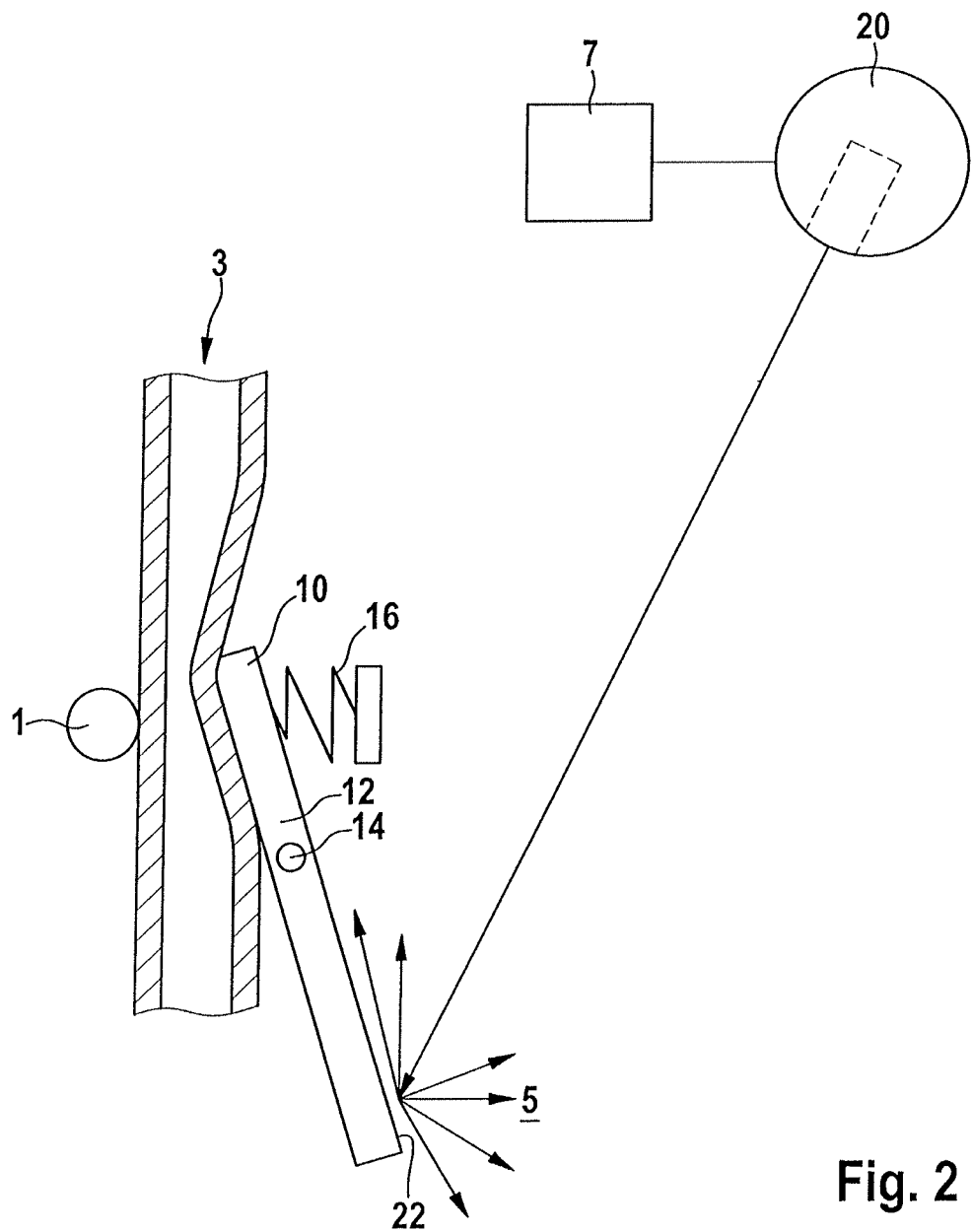
FIG. 2 shows another component in the form of a hose clip apparatus, which must be operated manually, having a system hose inserted.
Figure 3:
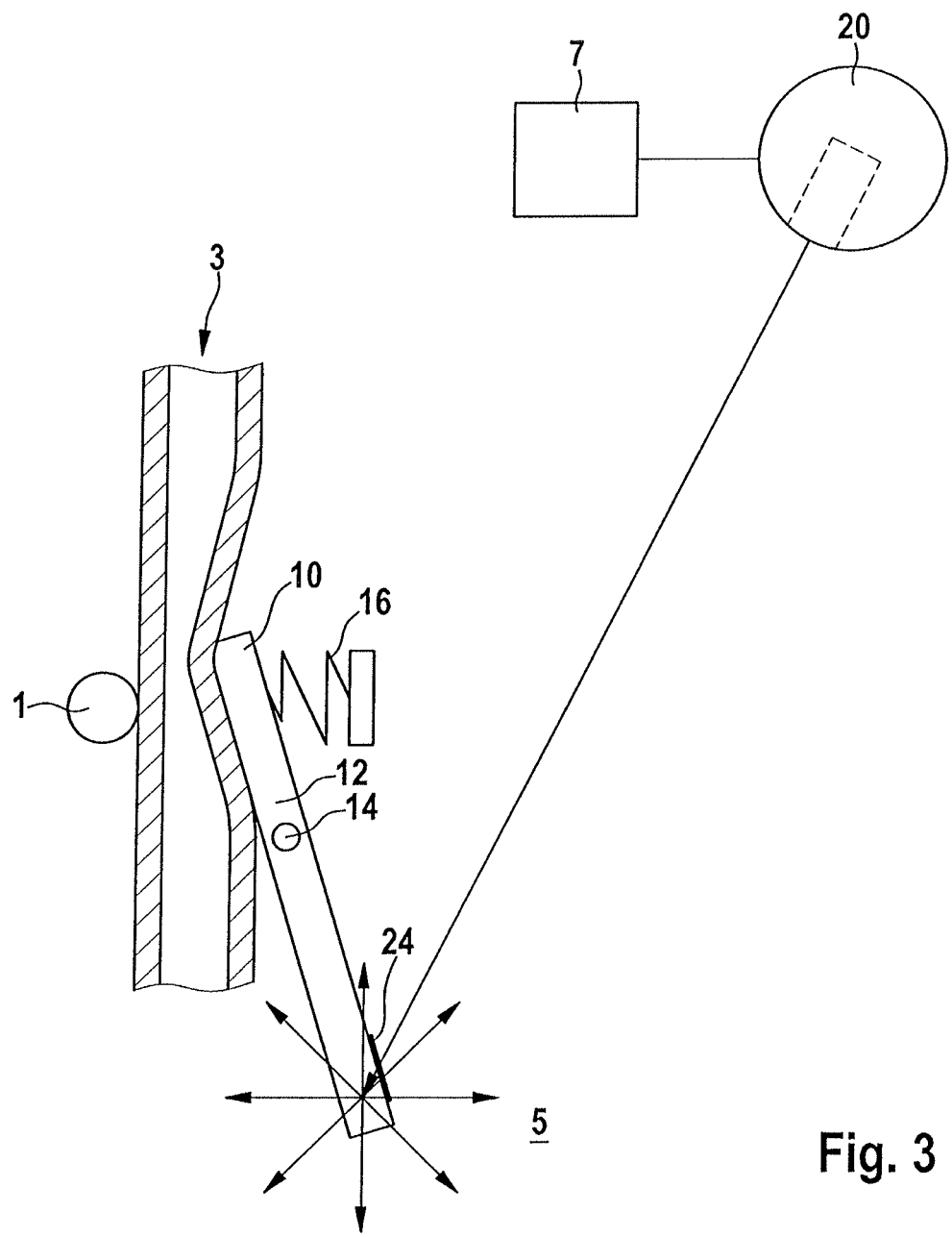
FIG. 3 shows an alternative embodiment of the hose clip apparatus shown in FIG. 2.

FIG. 3 shows a variant of the apparatus shown in FIG. 2. This time, the clip lever 12 is formed from a semitransparent material so that the projector 20, when it projects light onto the component, makes this so to say glow "from the inside" so that light 5 is in turn emitted from the clip lever 12 in turn, which is perceived at the operator as a signal for signaling the component to be operated. Semi-transparent component 12, in this example, may also be a component, which comprises a fluorescing material and the projector 20 may correspondingly emit a light signal in a wavelength range that excites the fluorescent material to fluoresce, however, is preferably not perceived by the human eye. Correspondingly, the operator does not perceive the light beam coupled into the clip lever 12 by the projector 20 but only the fluorescent light, which is emitted by the clip lever 12 as a response thereto.

To facilitate the coupling of the light beam that is emitted by the projector 20 into the component to be operated, i.e. the clip lever 12, this may be provided with an anti-reflex coating 24 at least at the region of the light entry surface.

Figure 4:
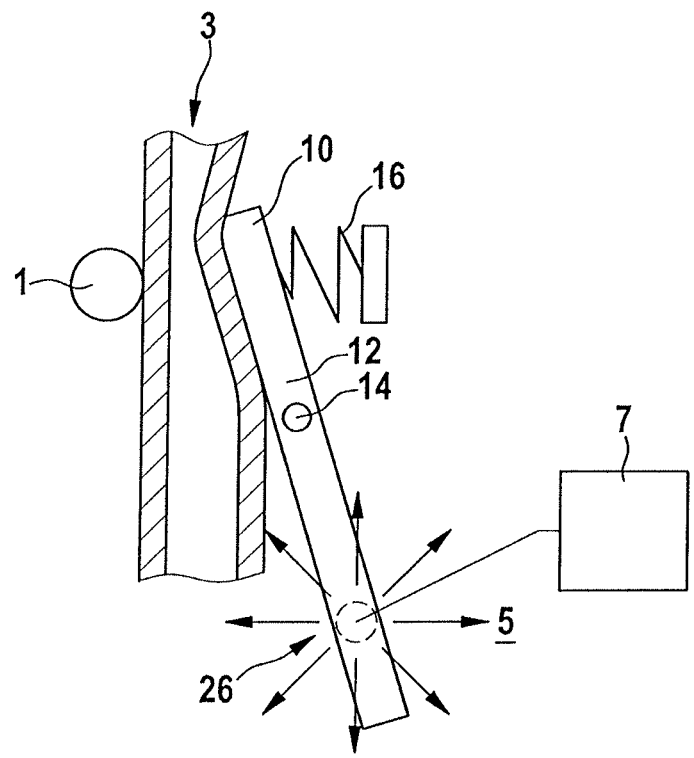
FIG. 4 shows a hose clip apparatus in another embodiment.

In the embodiment shown in FIG. 4, which corresponds to the clip levers shown in FIGS. 2 and 3 with respect to their mechanical construction, a light source 26 is provided in the clip lever 12 itself, for example, in the form of an LED, which may in turn be controlled via the control apparatus 7 whenever it should be signaled to the operator that the clip apparatus must be operated.

Figure 5:
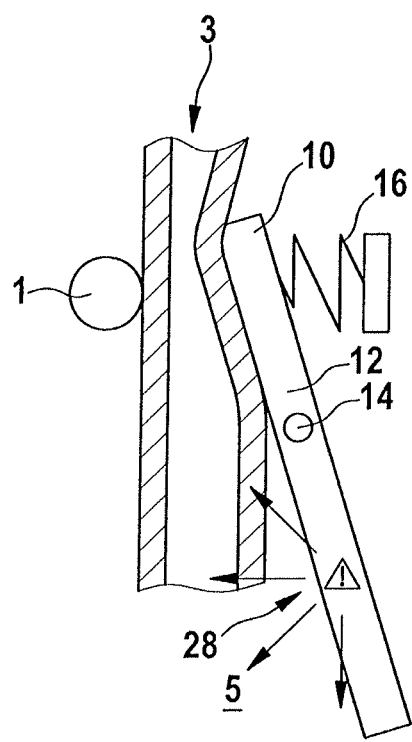
FIG. 5 shows another hose clip device with a signaling device.

FIG. 5 shows another embodiment in which an optical symbol 28 is applied on the clip lever 12. The symbol 28 may be applied in the form of a fluorescent material so that is starts to glow when it is irradiated with a corresponding light. The optical symbol may be applied in the form of a change in refractive index, for example, by selectively applying an anti-reflex coating, or it may be applied as a semitransparent or opaque material in such a way that the symbol 28 becomes visibly distinguishable for the operator when subjecting the clip lever 12 to light. In the case of fluorescence, the material correspondingly fluoresces; in the case of semitransparent material, the marking will be glowing brighter than the rest of the clip lever; in the case of an opaque material, the clip lever 12 will be glowing brighter than the symbol 28. In this context, it is achieved that the operator can clearly distinguish an optical symbol 28 on the clip lever 12.

In a preferred variant of the embodiment shown in the FIG. 5, different optical symbols 28 may be applied, preferably even at the same location of the component. These different optical symbols may, for example, be applied by means of different fluorescing materials of different properties so that when the component 12 is irradiated or excited with light of a first wavelength a first symbol glows and when the component 12 is irradiated with a second light or a light of a second wavelength respectively the second component glows.

Figure 6:
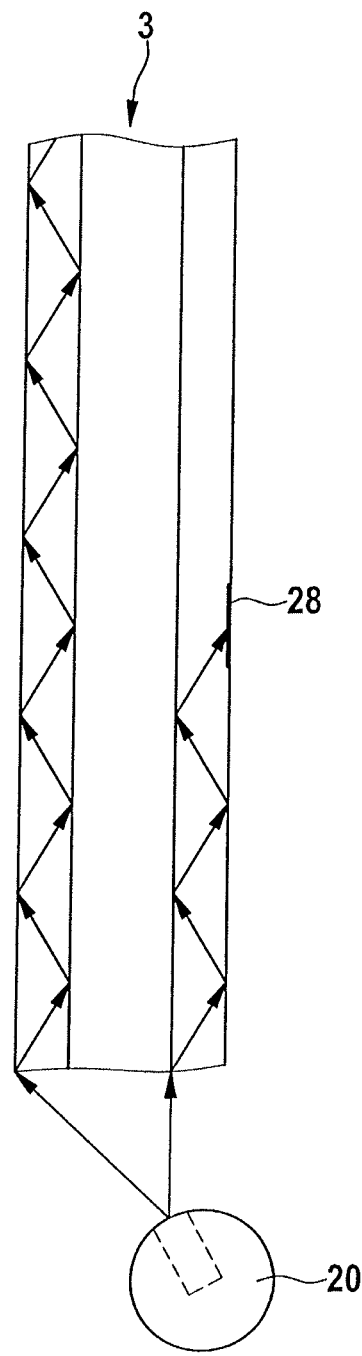
FIG. 6 shows a component in the form of a system hose schematically in cross sectional view and in top view.
Figure 7:
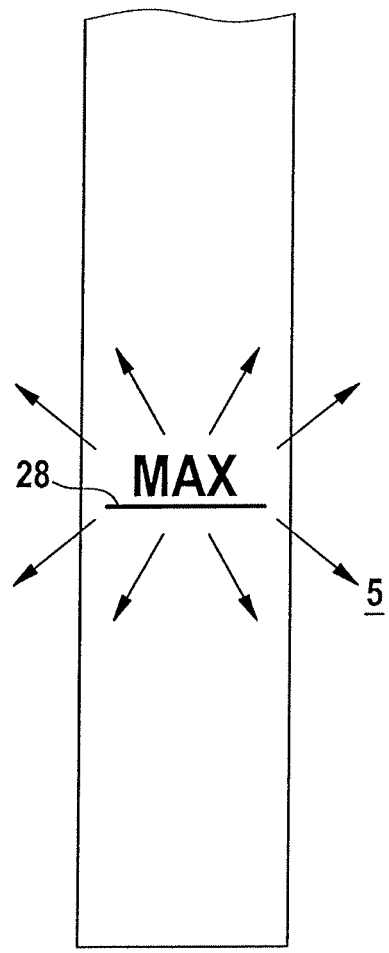
FIG. 7 shows a system hose of FIG. 6 in a sectional display.

The FIGS. 6 and 7 schematically show a system hose 3 in the form of a transparent or semi-transparent single-use hose into which light is coupled by means of a projector 20. It is known that the light that is coupled into a transparent material under a certain angle is totally reflected at the respective boundary surfaces and thereby results in the light guide effect shown in the FIG. 6 on the left side. By processing of the respective surface by means of a refractive index change, the light guided by the light guide may again be coupled-out. This is shown in particular in FIG. 7. This refractive index change for coupling-out an optical symbol 28 may be achieved, for example, by applying an anti-reflex material onto the surface of the single-use hose. Further, by simple milling or etching the surface may be roughened so that the incident angle does not allow a total reflection anymore and a part of the light is coupled-out accordingly.

Figure 8:
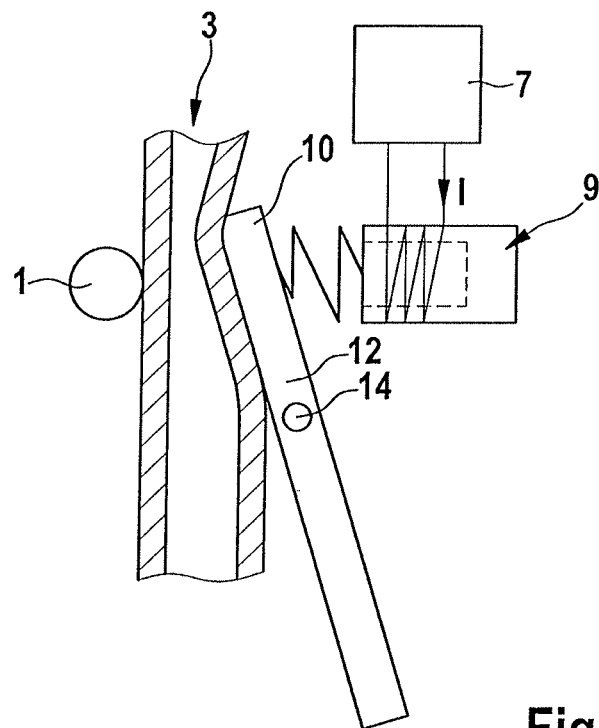
FIG. 8 shows a hose clip apparatus in another embodiment.

In FIG. 8, another variant of the clip apparatus 12 is schematically shown wherein an electrodynamic converter 9, through which a current I flows, is employed as a signaling device. Correspondingly, a current I may be then output to the electrodynamic converter 9 by the control apparatus 7 when a signaling is supposed to occur. The operator senses a vibration and may also, depending on the frequency of the current I, perceive an acoustical signal. Accordingly, in this variant, a haptical and/or acoustical signaling of the component to be operated may occur.

Figure 9:
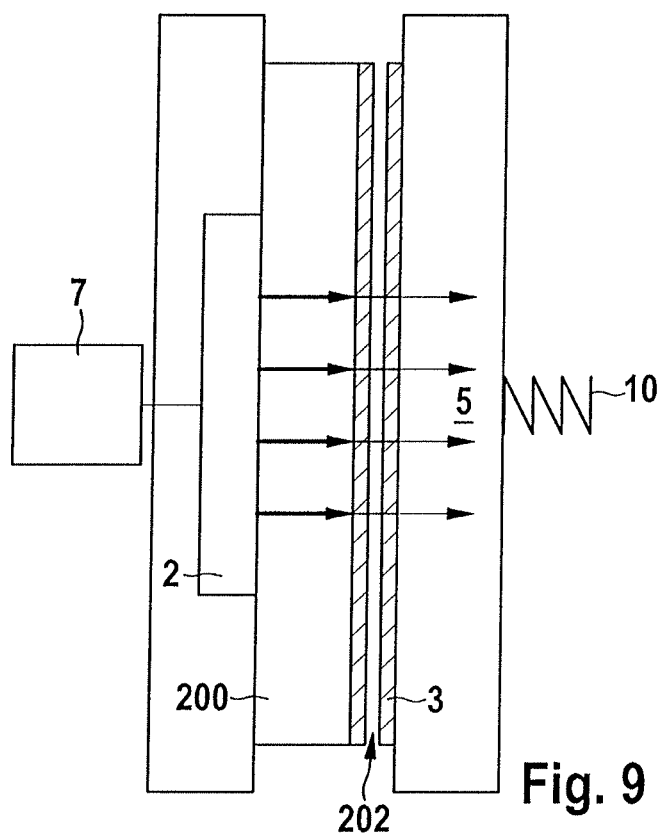
FIG. 9 shows an interface between a treatment apparatus and a single-use item.

FIG. 9 shows another embodiment in which a light source 2 radiates through a transparent cover 200 and through an air gap 202 into a single-use item 3, which is held by a clip apparatus 10. The illumination apparatus 2 correspondingly radiates through the single-use item 3 and is correspondingly controlled by the control apparatus 7. The single-use item 3 may preferably comprise a coating promoting the transmission, for example an anti-reflex coating, so that the radiating-through may occur with high efficiency.

For emitting a signal from a single-use item, an interface for coupling-in light is preferably provided at the single-use item into which light may be introduced into the single-use article and which is then further guided within the single-use article, which in this case serves as a light guide, and visibly emerges at a location specified at the single-use article, for example, by means of treatment of the surface of the light guide for changing the refractive index. The corresponding boundary surfaces, for example, at the interface or at the emerging location, may be provided with anti-reflex coating at the single-use article. On the single-use item, semi-transparent markings may be provided which are excited to glow by means of the light coupled into the single-use item. Such semi-transparent markings may preferably be designed so that they are excited to glow only at different wavelengths and, correspondingly, by means of the provision of multiple of such markings may be selectively controlled by coupling-in light of different wavelengths.

The signaling device may also comprise a non-visible light source which meets a fluorescent medium at the component to emit visible light at the component by means of fluorescence.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An apparatus for supporting an operator in operating a blood treatment apparatus, said apparatus comprising:
    a signaling device configured to signal a necessary operation of a component of the blood treatment apparatus that is to be operated, the component to be operated including as a part thereof the signaling device, such that a signal from the signaling device is emitted via the component to be operated,
    the signaling device including a light source provided in the component to be operated, or the signaling device including at least one of an electrodynamic converter and an electro-acoustic converter, which interacts with the component to be operated and/or is provided therein, or the component including a light guide or being configured as a light guide, with light being coupled into the component via the signaling device; and
    a control apparatus in communication with the component to be operated, the control apparatus being configured to control the signaling device based on the component operation to be performed,
    the necessary operation including at least one of preparing the blood treatment apparatus in an initial state prior to a treatment of a patient, and, following the treatment, resetting the blood treatment apparatus into the initial state for performing the treatment of another patient.

2. The apparatus according to claim 1, wherein the signaling device includes at least one of an optical, a haptical, and an acoustical signal generator for generating, respectively, at least one of an optical, a haptical, and an acoustical signal, and
    wherein the signal is generated as at least one of a symbol, a signal, and text.

3. The apparatus according to claim 1, wherein the signaling device includes a projector, which illuminates the component to be operated.

4. The apparatus according to claim 1, wherein the signaling device interacts with the component to be operated in order to emit the signal from the component.

5. The apparatus according to claim 1, wherein the signaling device is configured to activate at least one optical symbol provided at the component to be operated.

6. The apparatus according to claim 5, wherein the signaling device is configured to selectively activate at least two optical symbols arranged at the component to be operated.

7. The apparatus according to claim 1, further comprising a system monitor that monitors the blood treatment apparatus, wherein the control apparatus is connected with and correlated with the system monitor.

8. A medical device comprising an apparatus according to claim 1, the blood treatment apparatus being a dialysis device, a hemodialysis device, a hemofiltration device, a hemodiafiltration device, a peritonealdialysis device, or an apheresis device.

9. The apparatus according to claim 1, wherein the light source is an LED.

10. The apparatus according to claim 1, wherein the component to be operated is a single-use item.

11. The apparatus according to claim 1, wherein the blood treatment apparatus includes a mounting for holding a single-use system hose, wherein the signaling device signals the necessary operation of the system hose, wherein the control apparatus operates independently of an operator request, wherein the light source is arranged behind the system hose such that the light is incident on and/or emitted from the system hose, and wherein the light source at least partially illuminates the system hose when the light source is activated by the control apparatus to emit an optical signal from the system hose.

12. The apparatus according to claim 1, wherein the blood treatment apparatus includes a clamping device for clamping a system hose, wherein the clamping device includes a semi-transparent clamping lever, wherein the signaling device signals the necessary operation of the clamping lever, wherein the control apparatus operates independently of an operator request, and wherein the light source is arranged in the clamping lever such that the light is incident on and/or emitted from the clamping lever, and wherein the light source illuminates the clamping lever when the light source is activated by the control apparatus.

13. A method of supporting an operator in operating a blood treatment apparatus, said method comprising the steps of:
    signaling a necessary operation of a component of the blood treatment apparatus that is to be operated, the component to be operated including as a part thereof the signaling device, such that a signal from the signaling device is emitted via the component to be operated, the signaling device including a light source provided in the component to be operated, or the signaling device including at least one of an electrodynamic converter and an electro-acoustic converter, which interacts with the component to be operated and/or is provided therein, or the component including a light guide or being configured as a light guide, with light being coupled into the component via the signaling device; and with a control apparatus in communication with the component to be operated, controlling the signaling step based on the component operation to be performed, the necessary operation including at least one of preparing the blood treatment apparatus in an initial state prior to a treatment of a patient, and, following the treatment, resetting the blood treatment apparatus into the initial state for performing the treatment of another patient.

14. The method according to claim 13, wherein the emitted signal is at least one of an optical, an acoustical, and a haptical signal.

15. The method according to claim 13, wherein an optical symbol is emitted from the component to be operated.

16. The method according to claim 15, wherein the optical symbol is selected from at least two optical signals arranged at the component to be operated.

17. A single-use item for a blood treatment apparatus having a component to be operated by an operator, said component comprising:

a signaling device that signals a necessary operation of the component of the blood treatment apparatus that is to be operated, the component to be operated including as a part thereof the signaling device, such that a signal from the signaling device is at least one of an optical, an acoustical, and a haptical signal, and is emitted via the component to be operated, the signaling device including a light source provided in the component to be operated, or the signaling device including at least one of an electrodynamic converter and an electro-acoustic converter, which interacts with the component to be operated and/or is provided therein, or the component including a light guide or being configured as a light guide, with light being coupled into the component via the signaling device, the necessary operation including at least one of preparing the blood treatment apparatus in an initial state prior to a treatment of a patient, and, following the treatment, resetting the blood treatment apparatus into the initial state for performing the treatment of another patient, with the signaling device being controllable based on the component operation to be performed, and with a control apparatus being in communication with the component to be operated.

18. The single-use item according to claim 17, wherein the signaling device is the light source.

19. The single-use item according to claim 18, wherein the light source is at least one of an LED, an electrodynamic converter, and an electro acoustic converter.

20. The single-use item according to claim 17, wherein the component includes the light guide or is configured as the light guide, and wherein the light guide includes an interface for coupling-in light.

21. The single-use item according to claim 17, further comprising at least an optical symbol for emitting the optical signal.

22. The single-use item according to claim 17, further comprising at least two selectively activatable optical symbols for emitting the optical signal.

* * * * *